(12) United States Patent
Shen et al.

(10) Patent No.: US 7,004,955 B2
(45) Date of Patent: Feb. 28, 2006

(54) EMBOLIC FILTER

(75) Inventors: Christopher T. Shen, Stanford, CA (US); Olin Palmer, Mountain View, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 172 days.

(21) Appl. No.: 10/414,925

(22) Filed: Apr. 16, 2003

(65) Prior Publication Data

US 2003/0195554 A1    Oct. 16, 2003

Related U.S. Application Data

(63) Continuation of application No. 09/939,213, filed on Aug. 24, 2001, now Pat. No. 6,551,342.

(51) Int. Cl.
*A61M 29/00* (2006.01)
(52) U.S. Cl. .................................................. 606/200
(58) Field of Classification Search ............... 606/200, 606/113, 114, 127, 159, 198; 623/1.15, 1.16
See application file for complete search history.

(56) References Cited

U.S. PATENT DOCUMENTS

| | | |
|---|---|---|
| 2,943,626 A | 7/1960 | Dormia |
| 4,347,846 A | 9/1982 | Dormia |
| 4,611,594 A | 9/1986 | Grayhack et al. |
| 4,619,246 A | 10/1986 | Molgaard-Nielsen et al. |
| 4,865,017 A | 9/1989 | Shinozuka |
| 4,873,978 A | 10/1989 | Ginsburg |
| 4,969,891 A | 11/1990 | Gewertz |
| 4,990,156 A | 2/1991 | Lefebvre |
| 4,998,539 A | 3/1991 | Delsanti |
| 5,152,777 A | 10/1992 | Goldberg et al. |
| 5,171,233 A | 12/1992 | Amplatz et al. |
| 5,192,286 A | 3/1993 | Phan et al. |
| 5,234,458 A | 8/1993 | Metais |
| 5,330,482 A | 7/1994 | Gibbs et al. |
| 5,383,887 A | 1/1995 | Nadal |
| 5,486,183 A | 1/1996 | Middleman et al. |
| 5,496,330 A | 3/1996 | Bates et al. |
| 5,509,923 A | 4/1996 | Middleman et al. |
| 5,549,626 A | 8/1996 | Miller et al. |
| 5,601,572 A | 2/1997 | Middleman et al. |
| 5,681,347 A | 10/1997 | Cathcart et al. |
| 5,695,518 A | 12/1997 | Laerum |
| 5,709,704 A | 1/1998 | Nott et al. |
| 5,720,754 A | 2/1998 | Middleman et al. |
| 5,720,764 A | 2/1998 | Naderlinger |
| 5,792,156 A | 8/1998 | Perouse |
| 5,810,874 A | 9/1998 | Lefebvre |
| 5,820,628 A | 10/1998 | Middleman et al. |
| 5,895,398 A | 4/1999 | Wensel et al. |
| 5,902,263 A | 5/1999 | Patterson et al. |
| 5,904,690 A | 5/1999 | Middleman et al. |
| 6,053,932 A | 4/2000 | Daniel et al. |

(Continued)

*Primary Examiner*—Kevin T. Truong
(74) *Attorney, Agent, or Firm*—Fulwider Patton LLP (57) ABSTRACT

An intravascular filter device for use in capturing debris which may occur as a result of an intravascular procedure. The filter device includes a proximal section, a distal section and a mid-section. The mid-section includes three rings configured in a sixteen apices alternating V-pattern. The filter device specifically embodies structure that provides enhanced radial opening and angular resistance to collapse in its expanded state. While, in its compressed state the filter device provides an extremely small compressed profile giving it the desired ability to be delivered into very small vessels of the human vasculature.

10 Claims, 7 Drawing Sheets

U.S. PATENT DOCUMENTS 6,168,603 B1   1/2001   Leslie et al.
6,171,327 B1   1/2001   Daniel et al.
6,402,771 B1 *  6/2002   Palmer et al. .............. 606/200
6,443,972 B1 *  9/2002   Bosma et al. ............... 606/200

* cited by examiner

EMBOLIC FILTER

This application is a continuation of U.S. application Ser. No. 09/939,213, filed Aug. 24, 2001 now U.S. Pat. No. 6,551,342.

BACKGROUND OF THE INVENTION

The present invention relates generally to intravascular devices and systems and more particularly, filter devices which can be used to capture embolic material or thrombi found in blood vessels.

The intravascular filter device and system of the present invention is particularly useful as a passive device utilized when performing balloon angioplasty, stenting procedures, laser angioplasty or atherectomy in critical vessels where the release of embolic debris into the bloodstream can occlude the flow of oxygenated blood to the brain or other vital organs, which can cause devastating consequences to the patient. While the filter device and system of the present invention is particularly useful in the cerebral vasculature and neuro-vasculature, the invention can be used in conjunction with any vascular interventional procedure in which there is an embolic risk.

A variety of non-surgical interventional procedures have been developed over the years for opening stenosed or occluded blood vessels in a patient caused by the build up of plaque or other substances on the wall of the blood vessel. Such procedures usually involve the remote introduction of the interventional device into the lumen of the artery, usually through a catheter. In typical carotid PTA procedures, a guiding catheter or sheath is percutaneously introduced into the cardiovascular system of a patient through the femoral artery and advanced, for example, through the vasculature until the distal end of the guiding catheter is in the common carotid artery. A guidewire and a dilatation catheter having a balloon on the distal end are introduced through the guiding catheter with the guidewire sliding within the dilatation catheter. The guidewire is first advanced out of the guiding catheter into the patient's carotid vasculature and is directed across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent is crimped tightly onto the balloon portion of the catheter and transported in its delivery diameter through the patient's vasculature. At the deployment site, the stent is expanded to a larger diameter, often by inflating the balloon portion of the catheter.

Prior art stents typically fall into two general categories of construction. A first type of stent is expandable upon application of a controlled force, as described above, through the inflation of the balloon portion of a dilatation catheter which, upon inflation of the balloon or other expansion means, expands the compressed stent to a larger diameter to be left in place within the artery at the target site. A second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above minimally invasive interventional procedures, when successful, avoid the necessity of major surgical operations. However, there is one common problem which can become associated with all of these types of procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, cerebral vasculature, or neuro-vasculature, the release of emboli into the circulatory system can be extremely dangerous and sometimes fatal to the patient. Naturally occurring debris can also be highly dangerous to a patient. That is, debris which travels through the blood vessel as a natural result of bodily functions and not as a result of an intervention procedure. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments that naturally occur or that enter the circulatory system during or immediately following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

In addition, the retrieval of fragmented clot may be incomplete, also resulting in emboli and distal occlusions, and further, access through tortuous lumens may prove difficult. Laser-based disruption devices employ the photoacoustic effect to fragment clot. Local disruption may open up a proximal occlusion but also may cause significant distal emboli.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could otherwise cause problems to the patient's vasculature. Other techniques which have had some limited success include the placement of a prior art filter or trap downstream from the treatment site to capture embolic debris before it reaches the smaller blood vessels downstream. However, there have been problems associated with conventional prior art filtering systems as well. In particular, certain previously developed filtering devices do not optimize the area for embolic collection. That is, conventional filtering devices may not present a collection device that spans the entirety of the vessel or it may include supporting structure that itself impedes emboli collection. Certain other devices do not embody sufficient angular resistance to collapse.

Moreover, thrombectomy and foreign matter removal devices have been disclosed in the art. However, in addition to suffering from the same disadvantages as certain conventional prior art filter devices, such devices have been found to have structures which are either highly complex such as with multiple components or highly convoluted geometry or lacking in sufficient or effective expansion and retraction capabilities. Disadvantages associated with the devices having highly complex structure such as multiple components or highly convoluted geometry include difficulty in manufacturability as well as use in conjunction with microcatheters. Other devices with less coverage can pull through clots due in part to the lack of experience in using the same or otherwise lack an expanded profile that is adequate to capture clots or foreign bodies.

What has been needed is a reliable intravascular filter device and system for use when treating blood vessels. The filter device should be capable of capturing any naturally occurring embolic debris or that which may be released into the bloodstream during an interventional treatment, while minimizing the profile during delivery and maximizing coverage when deployed. The devices should embody an expanded profile that presents a consistent radial opening that completely occupies the vessel at the repair site as well as structure for effectively resisting collapse. Moreover, such devices should be relatively easy to deploy and remove from the patient's vasculature and also should be capable of being used in narrow and very distal vasculature such as the cerebral vasculature. The following invention addresses these needs.

SUMMARY OF THE INVENTION

Briefly and in general terms, the present invention is directed towards filter devices for capturing and removing undesirable material or objects which may occur during treatment, and thereby maintaining and restoring the patency of the blood vessel. The filter devices of the present invention are a linked or monolithic framework of thin struts that are radially expansible, and embodies a structure that provides a consistent radial opening as well as improved radial and angular resistance to collapse. That is, as the device is pulled such as through a vessel, the entrance thereto will not fall back or tip over. Moreover, the filter device maintains clearance in its interior space along its length allowing the undesirable materials or objects to enter and be captured.

In one aspect of the invention, the filter includes struts (members running both generally longitudinally and generally circumferentially) with very small widths and thicknesses and rings (circumferential members) with very small widths and thicknesses but large expansion ratios. Manufacturing, such as laser cutting or etching, the device from a piece of tubular stock facilitates creating the very small widths and thicknesses in the filter body. The body of the filter device is defined by a plurality of openings bounded by generally longitudinally and generally circumferentially extending members. A proximally extending member is attached to an elongate wire and the assembly is contemplated to be used in conjunction with a generally tubular delivery catheter. The filter device can be made from a tubular element or can be formed from a sheet which is rolled into a tubular shape.

The present invention provides a structure that has the capacity to capture and retain naturally occurring or foreign bodies while having a minimal profile that can traverse easily and repeatedly through a standard microcatheter across tortuous anatomy. The device embodies superior flexibility allowing it to be deployed and retrieved consistently across difficult anatomy while being able to retain captured material. The inner diameter of the device is heat-set to a pre-determined size. It is envisioned that there be a family of devices that have varying strut lengths, thicknesses, flexibility, and diameters as deemed appropriate for the specific type of vascular or non-vascular setting for which the device is to be used.

In a presently preferred embodiment, the filter device is self-expanding and includes a mid-section that forms a generally tubular profile. The proximally extending member projects as an axial extension of a line at the surface of the cylinder generally defining the substantially tubular portion to thereby provide an unobstructed opening at the proximal end of the filter. A terminal (i.e., distal) end of the filter device is constricted or closed so as to form a pocket for receiving emboli or thrombotic debris.

The filter device of the present invention can assume a number of different forms. In one presently preferred embodiment, the filter device embodies a first end portion, a second end portion, and a mid-portion having a plurality of consecutive rings, each ring having a plurality of generally straight members configured in an alternating V-pattern providing a plurality of proximal and distal apices on each ring. The generally straight members of the mid-portion rings that are configured in an alternating V-pattern may include a sixteen (16) apex design and therefore may require thirty-two (32) straight members. In another aspects, the filter device mid-section may includes rings having different lengths or, in the alternative, include a proximal section having different lengths. In the embodiments, the plurality of members can be curved, S-shaped, etc. rather than straight or can be a combination of straight and curved, etc.

Moreover, the present invention embodies a tip for an endovascular device including an atraumatic soft coil for preventing damage to tissue and facilitates advanceability. The tip further includes multiple layers of coiled material to enhance these objectives as well as to provide stiffness variations.

These and other objects and advantages of the invention will become apparent from the following more detailed description, when taken in conjunction with the accompanying drawings of illustrative embodiments.

DETAILED DESCRIPTION OF THE PREFERRED EMBODIMENTS

Figure 1:
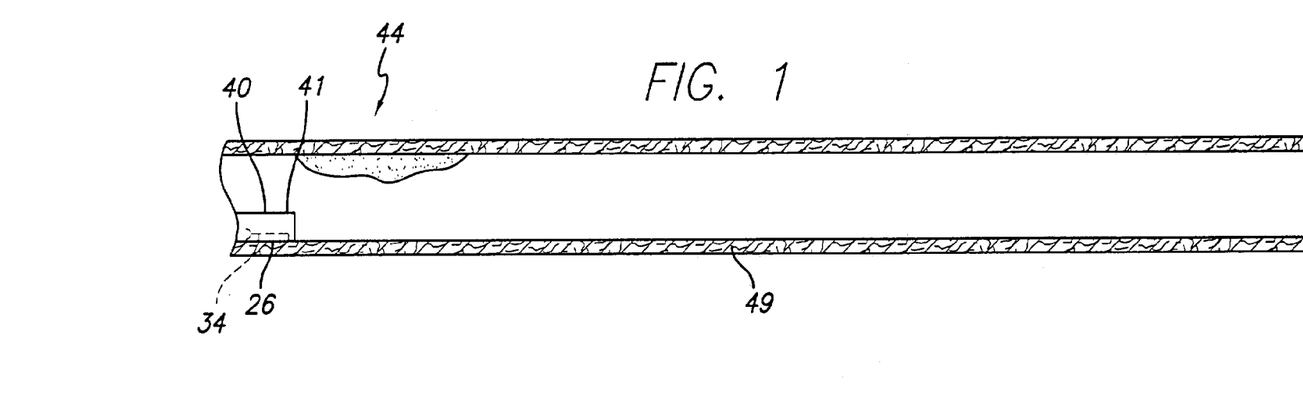
FIG. 1 is a side view, partially in cross-section, of a vessel partially occluded by a stenosis and a distal portion of a delivery catheter and intravascular filter device of the present invention positioned proximate the debris.
Figure 2:
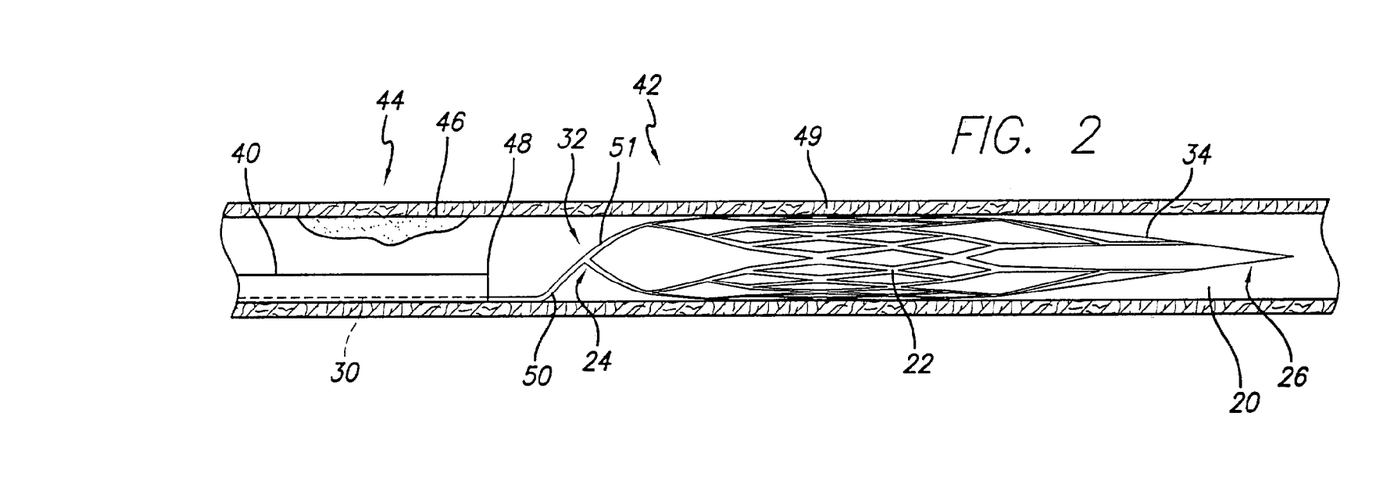
FIG. 2 is a side view, partially in cross-section, of the intravascular filter as deployed within the vessel of FIG. 1.

Referring now to the drawings, and in particular FIGS. 1 and 2, there is shown a filter device of the present invention. The filter device 20 is adapted to provide more consistent and improved radial opening as well as enhanced angular resistance to collapse. Moreover, the filter device 20 of the present invention is configured to facilitate the maintenance of clearance in its interior space along its length allowing undesired materials or objects found in the blood stream to enter and be captured.

Furthermore, since it is contemplated that the filter device 20 be manufactured from a tubular member to form elements with very small widths and thicknesses, the device is thus more easily packed to a relatively smaller diameter and inherently embodies high longitudinal flexibility.

The filter device 20 (FIG. 2) of the present invention includes a body 22 having a proximal end portion 24 and a distal end portion 26. The proximal end portion 24 is intended to be affixed to a terminal end portion of an elongate member 30 (i.e., wire; described in more detail below). In a presently preferred embodiment, the body 22 of the filter device 20 is generally tubular with a proximally directed opening 32 and a generally closed terminal end 34 to thereby form a filter for receiving embolus, stones, thrombus and foreign bodies found in vasculature, which may be free flowing within the blood stream during or as a result of treatment.

The filter device 20 for intravascular uses is contemplated to be used in conjunction with a generally tubular delivery catheter 40, such as a microcatheter. Additionally, it is contemplated that a conventional guide catheter (not shown) be used in combination with the delivery catheter 40 loaded with a filter device 20. A guide catheter (not shown) is employed to provide a guide within a patient's vasculature through which the delivery catheter 40 is inserted. A proximal end of the guide may have attached a rotating hemostatic valve fitted with sealing hemostatic valves. The filter device 20 is intended to be self-expandable, however, it is possible to employ an expandable member such as a balloon catheter (not shown) to radially expand a filter device that is not self-expandable, but rather must be deformed to assume an expanded configuration.

In use, the body 22 of a filter device 20 is inserted proximally in a compressed configuration coaxially within an internal bore of the generally tubular delivery catheter 40. The longitudinally extending elongate member 30 which is attached to the proximal end 24 of the body 22, is likewise coaxially received within the delivery catheter 40. Both the body 22 and elongate member 30 are slidable within the delivery catheter 40 and accordingly, the delivery catheter 40 and the filter device 20 can be displaced longitudinally with respect to each other.

A typical procedure will now be described. In order to ensure patency in a vessel during treatment, the filter device/delivery catheter assembly 42 is introduced into a patient's vasculature using conventional means such as the Seldinger technique. Sometimes, a cutdown is made to gain access to the patient's vasculature. Using standard endovascular techniques, the treatment area 44 in the vasculature is located. The treatment area 44 is crossed with the delivery catheter 40 and an appropriate guidewire (not shown). If angiographic mapping was not possible prior to crossing the treatment area, contrast is injected distal to the occlusion to map the distal vessels. The tip 41 of the delivery catheter 40 is positioned one device length or slightly more downstream of the treatment area 44 where blood will naturally flow across the device. The guidewire is removed and the filter device 20 is loaded through a rear hub (not shown) of the delivery catheter 20 with the assistance of an introducer sheath (not shown). The filter device 20 is advanced 30–40 cm and the introducer sheath is then removed.

Next, the filter device 20 is deployed into the diseased vessel by advancing the filter device until the distal tip 26 of the filter is positioned at the distal end of the delivery catheter 40. The filter device 20 is held in place by the operator holding the elongate member 30 still while the catheter 40 is retracted to allow the filter device to expand. Holding the filter device 20 in place, the catheter 40 is pulled back and removed from the patient allowing the filter 20 to be deployed at a position slightly downstream of the treatment site 44 to capture any free flowing emboli which may occur during subsequent treatment. Once complete, i.e., performance of the treatment is complete and any free flowing emboli is contained within the filter device 20, the filter is resheathed or partially resheathed into the guide catheter or a recovery catheter and retracted out of the patient's vasculature.

In one embodiment, during retraction of the system 42, the system is drawn back until the distal end of a proximal device marker coil (described below) is at the tip of the guide. At this point, a large syringe, perhaps 60 cc, is attached to the guide catheter at the rotating hemostatic valve on the hub. The guide catheter is aspirated as the filter device 20 and any captured emboli are drawn into the guide. Aspiration is maintained until the filter device 20 is fully into the rotating hemostatic valve of the guide catheter, but the filter device 20 is not yet drawn through the hemostatic valve. The rotating hemostatic valve is detached and removed with the filter device in it, allowing a moment of bleed back through the guide to flush any loose emboli. Optionally, then a second rotating hemostatic valve is attached to prevent excessive bleed back. The guide is then flushed with saline.

The manner in which the body portion 22 of the filter device 20 self-expands within the vasculature and the resultant expansion profile provides a number of advantages. In particular, the body 22 expands to conform to the diseased vessel at a position slightly adjacent to the repair site 44. That is, the generally tubular profile of the body portion 22 substantially conforms to the walls defining the blood vessel 49, therefore, any free flowing emboli dislodged into the blood during an intravascular operation may be completely captured within the deployed filter 20. Moreover, the expansion of the body 22 facilitates the maintenance of clearance in its interior space along its length allowing the material or objects 46 to freely enter and be captured and specifically provides a substantially unobstructed access to the proximally directed opening 32 to the body 22. Significantly, as the body 22 self-expands, members 50 and 51 leading to the opening 32 to the body 22 are angled or oriented so as to be adjacent the walls defining the blood vessel 49 and are therefore substantially removed from the flow path to thereby provide an unobstructed opening 32.

In its expanded state, the filter device 20 is particularly well-suited to capture and remove free flowing embolic or thrombotic debris from the diseased blood vessel 49. Once the intravascular treatment has been completed and any debris resulting therefrom has been captured within the filter device 20, the system 42 can be removed from the patient's vasculature or the filter device 20 containing the debris 46 can first be pulled within the guide catheter (not shown) and then the assembly 42 removed from the target repair site 44. Also, just the proximal end portion 24 of the filter device 20 can be cinched down to lock the debris without being fully pulled into the delivery catheter 40.

It is to be understood, however, that thrombus or other blood-based material captured within the filter may be eliminated in a variety of ways. For example, the material may be drawn into the guide catheter with the aide of a suction applied to the guide catheter, and removed from the body. Also, these materials may be removed from the diseased vessel 49 and allowed to dissolve under natural or induced lytic processes. Alternately, the material may be inserted into other vasculature more tolerant of occlusion and released.

Referring now to FIGS. 3–7, there is shown a preferred pattern 52 of the filter device 20 of the present invention. As will be developed further below, it is contemplated that the filter pattern 52 be cut from a tubular member using a laser. Alternatively, the pattern can be made from a flat sheet of nitinol and rolled into a tubular basket body. As best seen shown as if it was cut longitudinally and unrolled to show its pattern in a flat configuration (FIG. 3), the filter pattern 52 includes a body 22 having a proximal section 24, a distal section 26, a mid-section 54 and an elongate member 30 extending proximally from the proximal end section 24.

Figure 3A:
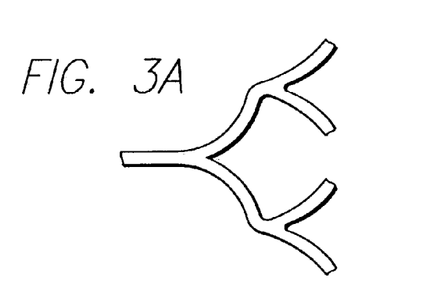
FIG. 3a is an enlarged view of a portion of the filter of the present invention, depicting an alternative embodiment of members defining the filter.
Figure 4:
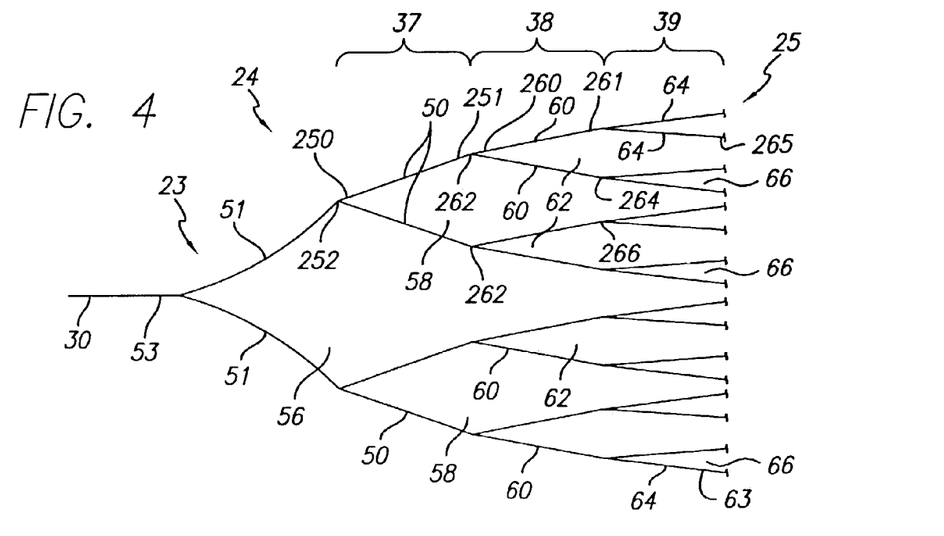
FIG. 4 is a plan view, depicting an enlarged proximal section of the intravascular filter of FIG. 3.

Referring in particular to FIG. 4, the proximal end section 24 has a proximal end 23 and a distal end 25 and includes a plurality of member sections 37, 38 and 39. Each member section includes a plurality of members or leashes 50, 60, and 64, respectively, which lead to and aid in defining an opening 32 (FIGS. 2 and 7) to the body 22, when in its tubular configuration. The members 50, 60, and 64 of each "member section" 37, 38, and 39 respectively, are pair-wise configured in a V-shape such that the proximal end of a member pair form the vertex of the V-shaped pair while the distal ends of each member pair form open ended end points for further distal connections. Therefore, the first member section 37 includes four generally straight members 50, each member having a proximal end 250 and a distal end 251. The generally straight members 50 are pair-wise in a V-shape with the proximal ends 250 forming a vertex 252 of the V-shape and the distal ends 251 forming the open ended branch end points of the V-shape. It is to be recognized that the members defining the body 22 of this or any other embodiment can have various shapes (See FIG. 3a). For example, the members can be curved, S-shaped, arced, or include straight portions or any combination of the same.

The second member section 38 is similarly configured as the first member section 37 having a plurality of generally straight members 60 also pair-wise configured in a V-shape. Each of eight (8) members 60 includes a proximal end 260 and a distal end 261. The proximal end 260 of the generally straight members 60 form vertices 262 and each vertex 262 is merged with one of the four distal ends 251 of the generally straight members 50 of the first member section 37.

Figure 3:
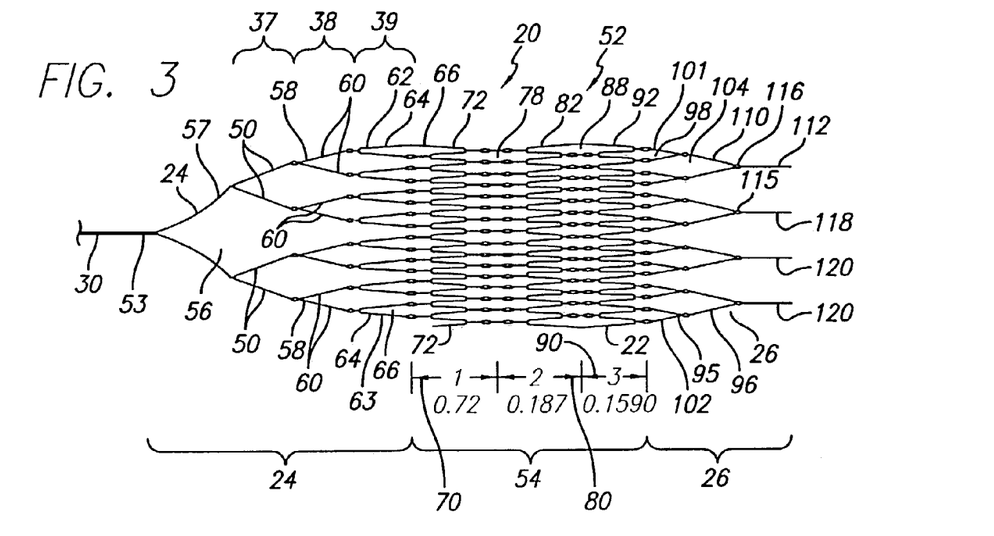
FIG. 3 is a plan view, depicting a pattern of a preferred embodiment of an intravascular filter of the present invention as if the filter was cut longitudinally and unrolled to show its pattern in a flat configuration.

Additionally, a third member section 39 is also provided having a plurality of generally straight members 64. Each of the sixteen (16) generally straight members 64 having a proximal end 264 and a distal end 265 are configured in the same fashion as the generally straight members 50 and 60 of the first member section 37 and second member section 38 in a pair-wise V-shape configuration. A plurality of proximal vertices 266 formed by the proximal ends 264 of the generally straight members 64 are merged with each of the eight distal end points 261 of the generally straight members 60 of the second member section 38. In this configuration, the distal section of the third member section 39 includes sixteen open-ended end points 265 between the body proximal section 26 and the body mid-section 54 (as shown in FIG. 3).

It is noted that the first, second, and third member sections 37, 38, and 39 of the proximal section 24 are configured to "fan-out" distally such that at each distal end of each member section, there is a doubling of the number of open-ended branch end points available for connection to successive member sections of the proximal section 24.

Therefore, at the distal end of the first member section 37, there are four open-ended branch end points 251, at the distal end of the second member section 38, there are eight open-ended branch end points 261, and finally, at the distal end of the third member section 39, there are sixteen open-ended branch end points 265. In this "fan-out" configuration, any desired number of end points at the distal end 25 of the proximal section 24 may be achieved by simply including more or less successive member sections. A sixteen (16) open-ended branch end point configuration was illustrated (as shown in FIG. 4) and described as having three member sections, however, for example, a proximal section having eight (8) open-ended branch end points, only two member sections are required and alternatively for a proximal section having thirty-two (32) open-ended branch end points, a forth member section will be required (not shown).

Figure 7:
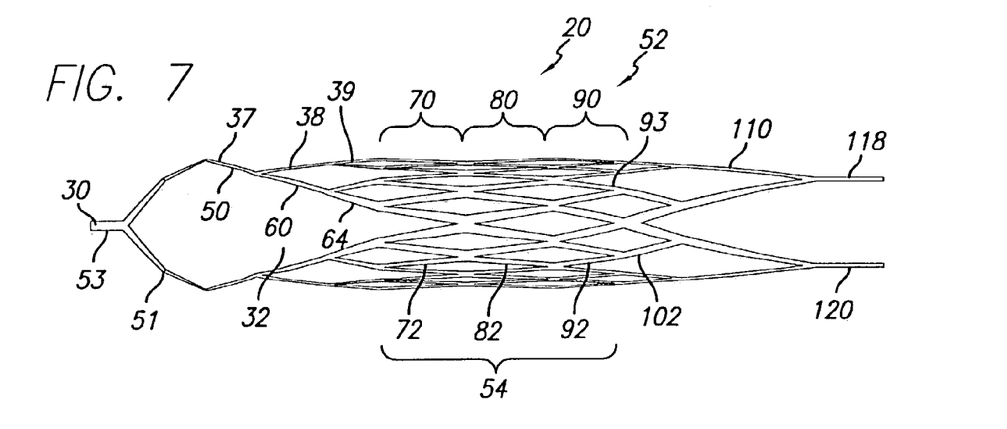
FIG. 7 is a perspective view, depicting a laser-cut configuration of the intravascular filter of FIG. 3.

The proximal end portion 24 further embodies a pair of connectors 51 extending proximally at an angle or in a curved fashion from the straight members 50 to thereby accomplish offsetting elongate member 30 from a central axis of the tubular body 22 of filter device 20 as best seen in FIGS. 2 and 7. The connectors 51, in turn, converge to form a proximally directed tab 53 that is connected to the elongate member 30. The straight members 50, 60, 64 and connectors 51 define a centrally located, generally diamond-shaped aperture 56, having a first length, that is substantially sandwiched between a plurality of diamond-like shaped proximal apertures 58, 62, and 66. The apertures 58, 62, and 66 each being progressively smaller in size and having progressively shorter lengths than the length of aperture 56 allow the filter device to "funnel" embolic or thrombotic debris into the filter body 22 where it is captured and retained. In its tubular configuration, a proximal convoluted ring 63 defined by members 64 is located and makes up the distal end 25 of the proximal end portion 24. The ring 63 provides for optimal radial opening to the filter body 22.

Figure 5:
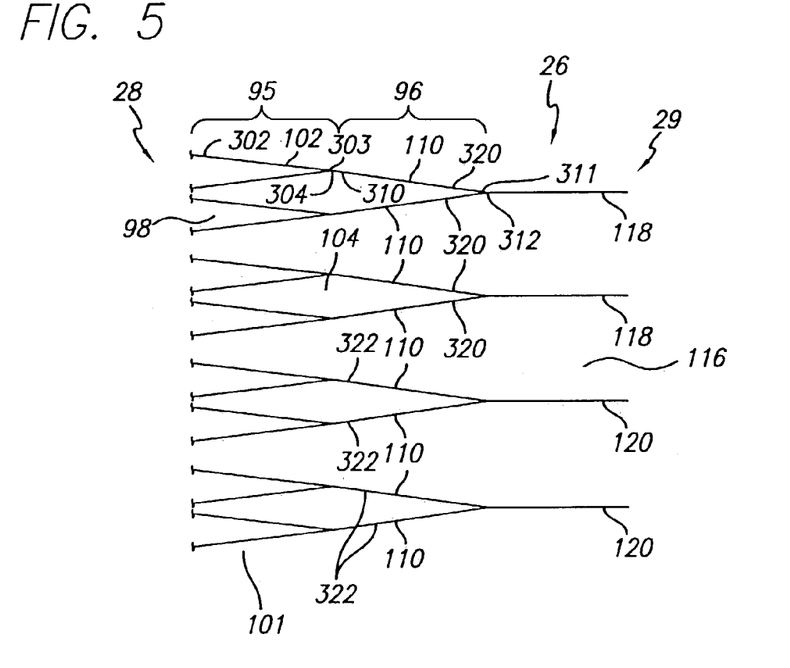
FIG. 5 is a plan view, depicting an enlarged distal section of the intravascular filter of FIG. 3.

Referring to FIG. 5, the device distal section 26 has a proximal end 28 and a distal end 29 and includes a plurality of member sections 95 and 96. Member section 95 includes a plurality of straight members 102 having a proximal end 302 and a distal end 303. Similarly member section 96 includes a plurality of straight members 110 having a proximal end 310 and a distal end 311. The straight members 102 and 110 of each member section 95 and 96 are pair-wise configured in a V-shape such that the proximal ends 302 and 310 respectively of each member pair form open-ended end points for connection with the distal vertices of the member section located proximally adjacent to it. In member section 95, distal ends 303 of a pair of straight members 102 converge to form a vertex 304 of the V-shaped pair. In the member section 96, distal ends 311 of a pair of straight members 110 converge to form a vertex 312 of the V-shaped pair.

Therefore, the first member section 95 includes sixteen (16) straight members 102. The straight members 102 are pair-wise in a V-shape with the proximal ends 302 comprising the open-ended branch ends of the V-shape and the distal ends 303 converging to form the eight-vertices 304 of the V-shape. The second member section 96 is similarly configured as the first member section 95 having eight (8) straight members 110 also configured in a V-shape. The proximal ends 310 of the straight members 110 form the open-ended branch ends of the V-shape and merge into each of the eight vertices 304 of the first member section 95. Pairs of the straight members 110 converge distally into four vertices 312, which are part of the distally directed straight members 118 and 120.

It is contemplated that the straight members 110 of the second member section 96 may be configured having different lengths. For example, of the eight (8) straight members 110 within the second member section 96, four straight members 320 may have a first length that may be longer in length than the other four straight members 322 having a second shorter length. In this configuration, two of the converging vertices 312 resulting from the shorter straight members 322 will be situated at a distance slightly shy of the vertices 312 resulting from the convergence of the longer straight members 320. The vertices 312 formed by the shorter straight members 322 merge into distally directed extensions 120 and the vertices 312 formed by the longer straight members 320 merge into distally directed extensions 118. It is contemplated that this staggered configuration will assist in closing off the terminal end 29 (distal end) of the filter (as will be discussed hereinafter.)

In this configuration, the first and second member sections 95 and 96 of the distal section 26 are configured to "fan-in" distally such that at each distal end of each member section, there is half the number of converging vertices available for distally successive member sections of the distal section 26. Therefore, moving distally from the proximal end 28 of the distal section 26, the straight members 102 of the first member section 95 includes sixteen proximal end points 302 and converge to form eight vertices 304 forming the distal end 303 of the first member section. The straight members 110 of the second member section 96 includes eight proximal end points 310 forming the eight vertices 304 of the first member section 95 and converge to form four vertices 312 forming the distal end of the second member section. Finally, the four distal vertices 312 of the second member section 96 converge to distally directed straight members 118 and 120.

The straight members 110 of the distal portion 26 define an open-ended, distally directed vee 116 sandwiched between a plurality of diamond-shaped apertures 98 and 104. A distal convoluted ring 101 defined by members 102 is located proximally adjacent the distal end portion 26 defining the distal end portion 26 proximal end 28. The ring 101 provides for maximal radial opening of the body 22. Distally directed extensions 118 and 120 project, in a parallel fashion, from the vertices defined by the plurality of converging straight members 110.

The distally directed straight members 118 and 120 of the filter distal portion 26 are joined together to form a substantially closed filter. This structure can be joined using soldering or by employing a coil (as will be described hereinafter) that is wrapped about the distally directed extensions 118 and 120 to form a soft tip. The distally directed extensions 118 and 120 may also be trimmed to a desired length. Alternatively, as discussed above, because the distally directed extensions 120 extend from two shorter length vertices 312 of the second member section 96, they may be inserted (tucked) into the two longer vertices 312 of the second member section 96 (not shown). This insertion eliminates the need to include a further level of convergence leaving only two distally directed extensions 118.

Figure 6:
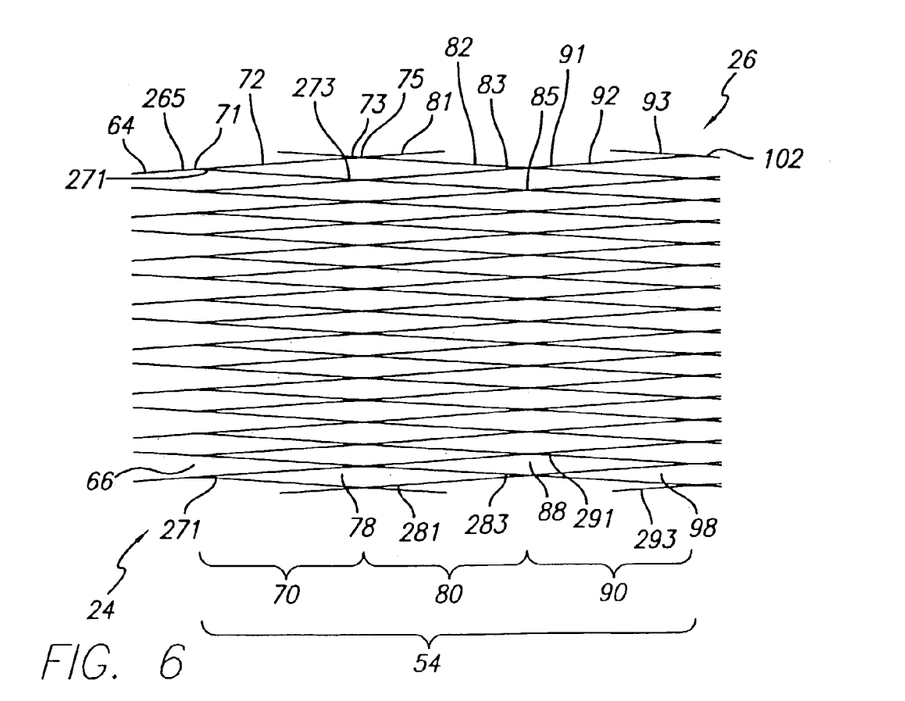
FIG. 6 is a plan view, depicting an enlarged mid-section of the intravascular filter of FIG. 3.

Referring to FIG. 6, the mid-section 54 of the filter pattern 52 includes generally a first ring 70, a second ring 80 and a third ring 90. In its manufactured form, the rings 70, 80, and 90 of the filter mid-section 54, together, form a generally tubular mid-section. Each ring 70, 80, 90 includes a plurality of straight members 72, 82, and 92 respectively. The straight members of each ring are in an alternating V-pattern configuration to form a plurality of apices defining a proximal end and a distal end of each ring. Hence, straight members 72 of the first ring 70 includes a plurality of apices 71 defining a proximal end 271 and apices 73 defining a distal end 273 of the first ring 70. Similarly second ring 80 includes proximal apices 81 and distal apices 83 and third ring 90 includes proximal apices 91 and distal apices 93. The rings meet each other at the apices, the first ring 70 meets the second ring 80 at connection 75 between distal apices 73 of the first ring and proximal apices 81 of the second ring. Similarly, the second ring 80 meets the third ring 90 at connection 85 between distal apices 83 of the second ring and proximal apices 91 of the third ring.

The filter mid-section 54 may join the filter proximal section 24 such that each of the distal end points 265 of straight members 64 of the filter proximal section 24 are joined at an angle to the proximal apices 71 of the first ring 70. Similarly, the filter mid-section 54 may join the filter distal section 26 such that the distal apices 93 of the third ring 90 are joined at an angle to the proximal open-ended end points 302 of the straight members 102 of the filter distal section 26. In this configuration, the filter proximal section 24, mid-section 54, and distal section 26 form a generally tubular filter device in its manufactured form (see FIG. 7).

It is contemplated that in one preferred embodiment, each distally successive alternating V-pattern ring 70, 80 and 90 may be configured to be shorter in length than the ring situated proximally to itself, for example ring 90 may be shorter in length than ring 80, which in turn, may be shorter in length than ring 70. The progressive shortening of ring lengths provides for a conical tapering of the filter from the proximal to the distal ends. This conically tapered configuration may enhance foreign body containment because the progressive shortening of the rings 80 and 90 translate into a progressive decreasing of the sizes of the apertures located within the distal portions of the filter mid-section 54, which, as discussed above, ultimately closes off at the filter distal section 26 to form a substantially closed filter device. Additionally, the tapered configuration may provide greater flexibility around bends found in the human vasculature.

Referring now to FIG. 7, the members 50, 60 and 64 form a tapered opening 32 to the generally tubular mid-section 54 with the elongate member 30 extending proximally from a sidewall defined by the mid-section 54. It is contemplated that the resultant tubular structure, in an undeformed state, includes a longitudinal axis that is parallel to both the elongate member 30 and the distally directed projections 118 and 120.

Another way to describe the basket device is that it begins with a proximal elongate member linked to a series of divergent branches of increased density covering varying fractions of the tubular circumference. The divergent branches wrap around the circumference from the side where the elongate member ends to form the tube. Linked from the divergent branches is one or more ring segments. Branching from the ring segment is a series of convergent branches covering varying fractions of the tubular circumference. This section is tapered down to the distal tip to reduce the required coverage area thus maintaining adequately small openings for encapsulation.

Although each of the first, second, and third rings 70, 80 and 90 of the body mid-section 54 have been shown as embodying a sixteen apex design having thirty-two straight members 72, 82, and 92 respectively, configured in an alternating V-pattern, as will be described below, designs having fewer or more apices with fewer or more straight members are contemplated. Such design modifications may produce enhanced qualities for the desired uses of the current invention and it will be understood that such modifications in the filter design will not depart from the scope of the present invention.

The porosity of the filter can be varied by increasing or decreasing the length and number of straight members of each ring 70, 80, and 90. In some instances there may be a need or desire to capture smaller foreign matter or emboli, therefore, it may be desirable to decrease the porosity of the filter for use under such circumstances. In order to decrease the porosity of the filter, either the lengths of the straight members of each ring 70, 80, and 90 may be decreased, or the number of straight members may be increased. As discussed above, by increasing the number of straight members, the body mid-section may result in a design having a higher number of apices.

Moreover, in any alternative design there need not be straight members 50, 60, and 64, extending from each proximal apices 71 of the first ring 70. It is necessary, however, that as with the ring design depicted, the modified pattern also result in rings that provide a complete open deployment consistently and reliably. To wit, such rings do not fall back. That is, there is no angular deflection when the structure is engaged upon a clot or foreign body.

In order to have the device collapse evenly, all continuous (not recursive) paths from the first divergence to the last convergence of members can be of approximately the same length. In that way, during collapse less buckling may occur in the longer members and the shorter members may not be required to stretch to achieve a substantially linear constrained configuration.

Figure 8:
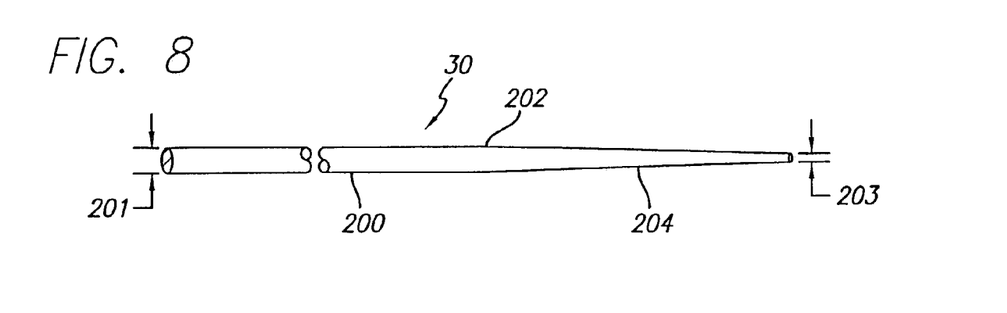
FIG. 8 is a plan view, depicting an elongate member of the present invention.

Referring now to FIG. 8, there is shown one preferred embodiment of the elongated member 30 of the present invention. The member 30 embodies a gradual or step-tapered core comprising a proximal section of 304V stainless steel and a distal section of nitinol or an equivalent material for the intended purpose. A proximal portion 200 of the member 30 has a generally constant cross-sectional profile and a first diameter 201. At a transition point 202, the member 30 begins to taper in a gradual and consistent, manner, or alternatively in a step-tapered or in a parabolic or other non-linear manner, from the first diameter 201 to a second diameter 203 along a distal end portion 204.

Figure 9:
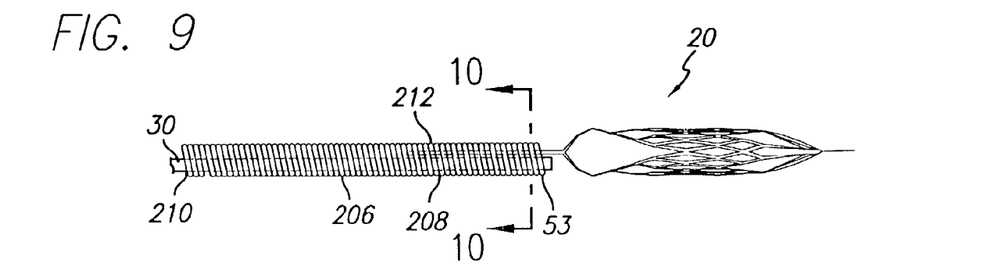
FIG. 9 is a side view, partially in cross-section, depicting a plurality of coils configured about a distal end portion of the elongate members in combination with a filter device of the present invention.
Figure 10:
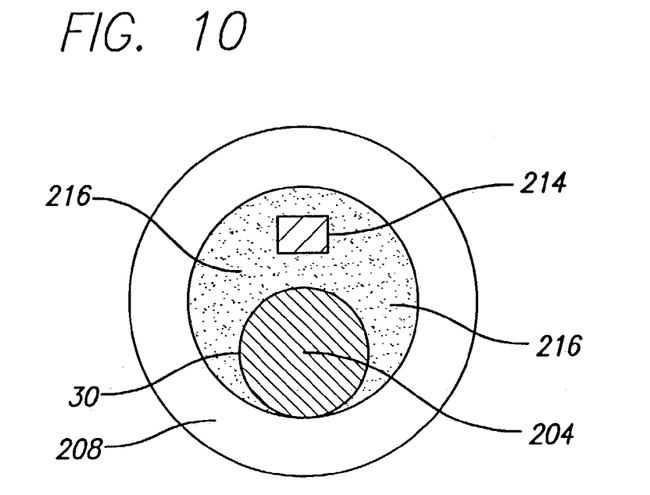
FIG. 10 is a cross-sectional view, depicting the assembly of FIG. 9 taken along lines 10—10.

As shown in FIGS. 9 and 10, a pair of longitudinally adjacent arranged coils 206, 208 are employed to attach a proximal tab 53 of a filter device 20 to the distal end portion 204 of the elongate member 30. The first, proximal coil 206 is contemplated to be composed of 304V stainless steel, the first coil being soldered to the elongate wire 30 near its tapered portion 210. The second coil 208 is contemplated to embody a medical grade radiopaque wire, typically a platinum alloy such as about 90% platinum and 10% iridium alloy. This second coil 208, which serves as a radiopaque marker, is soldered to the elongate member 30 near a distal end portion 212 of the first coil 206. Alternatively, the second coil 208 is soldered to the first coil 206. A proximal tab 53 of the filter device 20 is contained within the second coil 208 and is soldered 216 to the elongate member 30. (FIG. 10).

Figure 11:
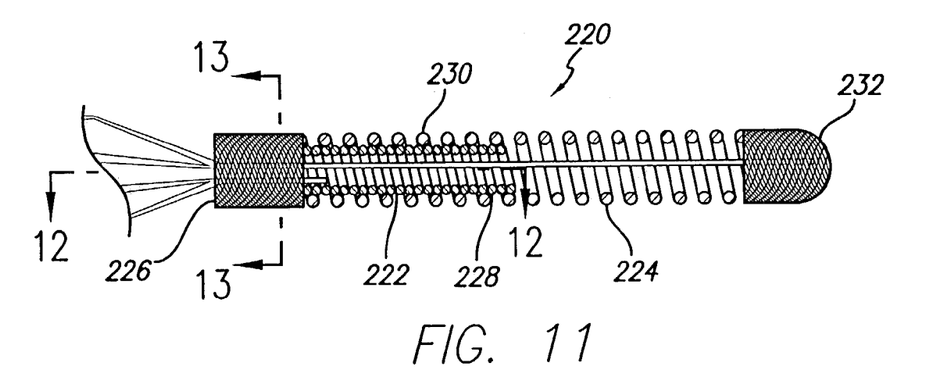
FIG. 11 is a side view, partially in cross-section, depicting a distal end portion of a tip of the filter device of the present invention.
Figure 12:
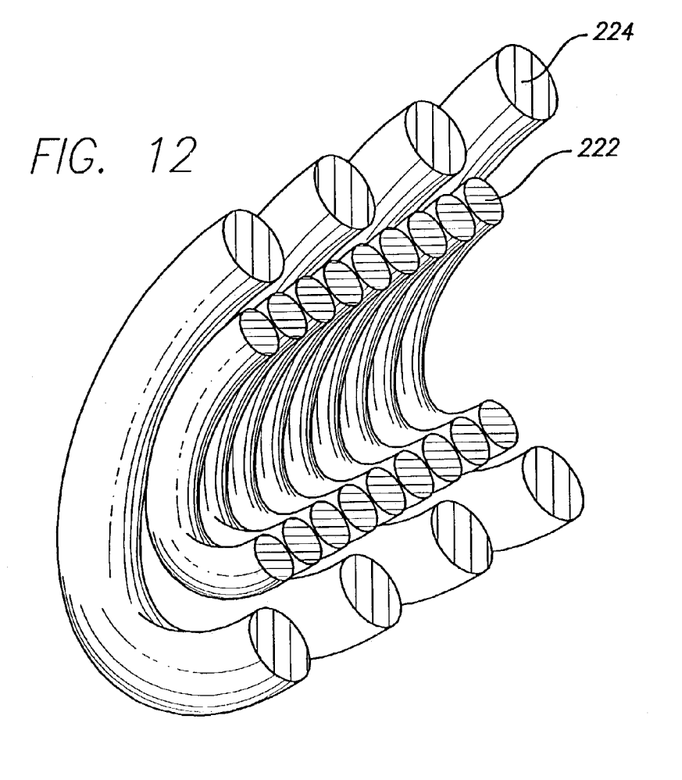
FIG. 12 is a cross-sectional view, depicting a portion of the assembly of FIG. 11 taken along lines 12—12.
Figure 13:
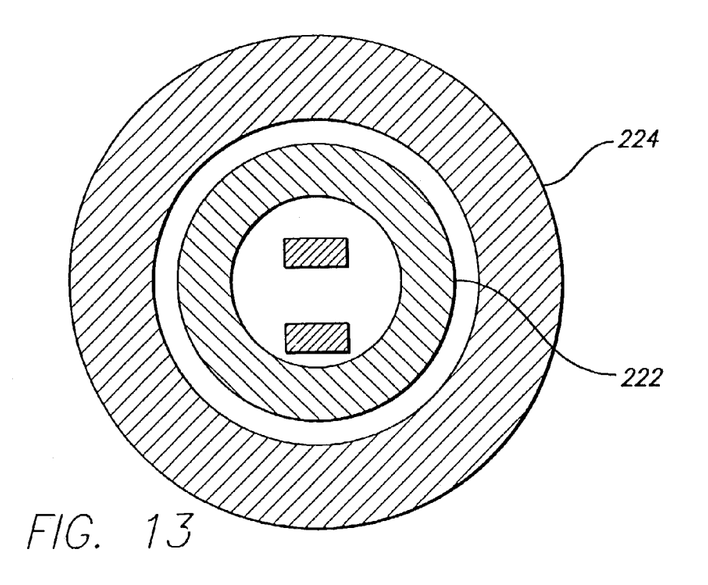
FIG. 13 is a cross-sectional view, depicting the assembly of FIG. 11 taken along lines 13—13.

Turning now to FIGS. 11–13, one presently preferred embodiment of a distal tip portion of the filter device 20 of the present invention is described. The distal tip portion embodies two partially coaxial coils 222 and 224, the combination of which retains the distally directed extensions 120 and 118 projecting from the body of the filter device 20 (see FIG. 7). The combination also provides a soft atraumatic tip with variable stiffness from softest distally to stiffer proximally. It is to be recognized that by varying the length of the tip and/or the coils 222, 224, changes in stiffness can be achieved to produce a tip with a desired flexibility.

The inner coil 222 is comprised of nitinol or equivalent material, and begins at a proximal location 226 and extends to a distal location 228. The nitinol inner coil 222 provides kink resistance as well as creates a smooth stiffness transition from the tip of the filter portion of the filter device 20. The outer coil 224 is coaxially configured about a distal portion 230 of the inner coil 222 and is preferably comprised of 90% platinum and 10% iridium alloy or an equivalent combination of materials. As such, the outer coil 224 can operate as a radiopaque marker. The distal tip portion 27 further includes a rounded terminal end 232 that provides a blunt atraumatic surface. The terminal end 232 embodies a soldered joint which acts in retaining the helical configuration of the outer coil 224.

Figure 14:
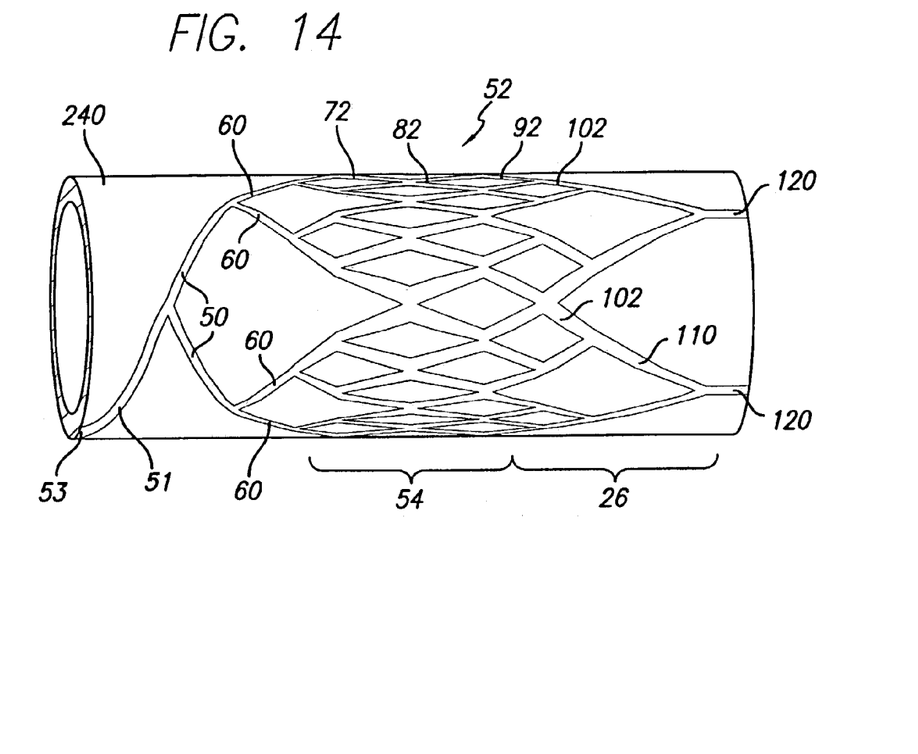
FIG. 14 is a perspective side view, depicting the filter device pattern projected onto the tubing from which it will be cut to produce the filter device of FIG. 3.
Figure 15:
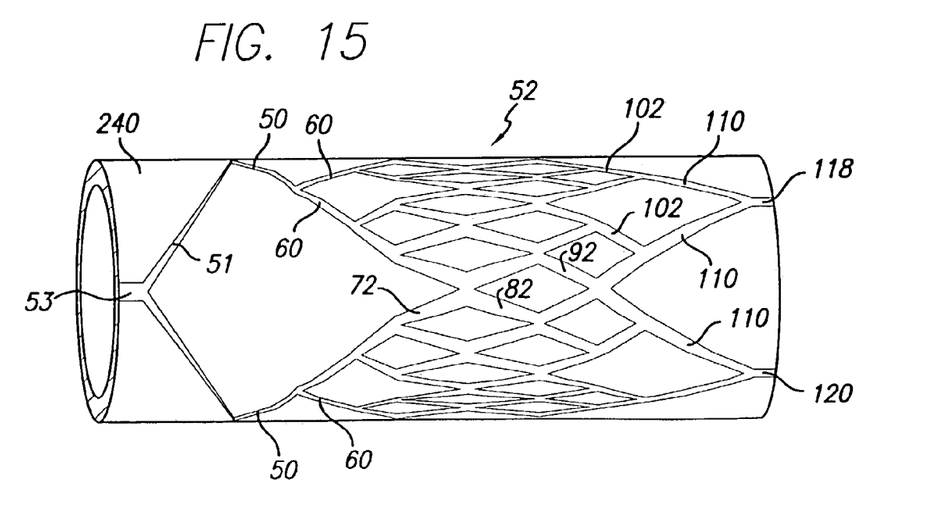
FIG. 15 is a perspective bottom view, the filter device pattern projected onto the tubing from which it will be cut from to produce the filter device of FIG. 3.

With reference to FIGS. 14 and 15, a brief summary of the process used to manufacture the filter devices 20 of the present invention will be discussed. As shown in FIG. 7, the preferred embodiment in its as cut configuration is relatively similar to the other alternative embodiments discussed above and includes a sixteen (16) apex, three ring pattern 52. It is contemplated that the filter devices 20 of the present invention be cut from a tube 240 (FIGS. 14 and 15) using a laser. In particular, a specific pattern is programmed into the laser device and the laser is activated to cut the desired pattern into the tubular element 240. The excess tubular components are removed, thereby leaving a manufactured structure such as the filter pattern 52 shown in FIGS. 14 and 15, corresponding to the desired pattern. In a presently preferred embodiment, a super elastic material such as nitinol may be a material of choice for the filter device 20. Thereafter, post-processing such as surface treatment, burr removal, oxide removal, and shape setting of the manufactured structure is performed. Heat treating is also performed for stress relief of the device.

In particular, post-processing steps include taking an as-cut device and bead blasting the device with aluminum oxide blasting media. The device is then inspected under a microscope for residual slag. If slag remains, the device is bead blasted again. Thereafter, the device is stress-relieved in a molten salt bath without expanding. The device is subsequently heat-expanded in a molten salt bath mounted on a suitable size mandrel. After heat expansion, surface oxidation is removed in an aqua regia bath. When nitinol is the material of choice, the nitinol is etched with HF solution to desired strut size resulting in desired softness. The device is then mounted on a guidewire, using coils and solder.

In the case of the pattern 52, the post-processing may include deforming the pattern 125 and then joining together the distally extending members 118 and 120 for the purpose of achieving a closed filter for receiving and containing debris found in the patient's vasculature. Being so configured, the pair of diverging members 50 define an opening to the resultant filter and the elongate member 30 extends from a sidewall defined by the opening.

The filter devices of the present invention provide improved radial opening compared to prior art filter devices since in an expanded state, the elongate member 30 is positioned substantially out of the flow path. Additionally, the current invention embodies improved resistance to radial and axial loads as compared to prior art filter devices. Moreover, since less deformation is required to produce a desired filter pattern, in that, angles between members are provided by laser cutting rather than from local deformations, for example, there is potentially improved stress distribution along the filter devices of the present invention compared to prior art filter devices. Additionally, a greater reduction in radial profile can be achieved without sacrificing performance and in particular, the device can be used in conjunction with microcatheters. As such, the filter devices 20 of the present invention can be passed through narrow and tortuous vasculature. The applications of the present invention are more widespread than that of conventional filter devices because of greater retrieval and capture characteristics while retaining the deliverability characteristics.

The above described invention is principally conceived to be operational during treatment of vessels, for use in capturing and maintaining for the purpose of displacing and/or removing material either foreign or native to the body, which may occur during or as a result of intravascular treatment within intraluminal or extraluminal spaces of the body including but not limited to intravascular and/or intra-arterial regions of the cerebral vasculature. The purpose of the device is to ensure and maintain functionality of the luminal space or systems dependent on the particular luminal space or as a method of producing any desired effect associated with the removal or displacement of undesirable material.

The intended delivery of the disclosed invention is by means of a commercially available catheter selected for its ability to access the desired location of engagement. The invention may be optimized for specific locations or uses by means of sizing the individual elements in the design and/or the overall dimensions, as well as selection of materials, mesh configuration, number and relative geometry of component members to meet the requirements of the operational space. Optimizations may include variations of the dimensions of length, thickness, and width of distal and proximal tabs for joining filter with delivery wire and distal tip to provide smooth stiffness transitions from tip to filter and filter to delivery wire. Such optimizations are means of adjusting operational attributes including: flexibility, applied circumferential force, engagement effectiveness, deliverability and traversal through tortuous vasculature, and volume of material to be engaged.

Alternate or additional materials for the filter portion of the device may include a shape memory polymer, thermoset, elastomer, thermoplastic constituents such as nylon, or other metal either pure or alloyed, as well as composite materials such as a combination of glass, aramid, or carbon in a binding matrix. A secondary mesh of the same or dissimilar material may be added to the filter. The wire portion of the device can alternatively be made from a single metal or combination of metals for kink resistance and high flexibility. Either or both components may be tapered to give a transition in stiffness that is appropriate for the vessel in which the invention is to be delivered. The distal tip of the device may incorporate concentric coils made of nitinol, stainless steel, or other metal or plastic to provide a soft flexible atraumatic end. As stated, the members defining a body of the disclosed devices can have various shapes including but not limited to curves, arcs, S-shapes, partial straight sections or any combination thereof. The same can be used to achieve desired or enhanced compression or deployment characteristics.

An alternate method of manufacture of the filter portion of the device may be photo-etching, or metal or polymer injection molding or water jet cutting. Furthermore, the device may employ any combination of coatings, agents, or features including those that result from material addition or subtraction to create grooves, bumps, three dimensional patterns, and textures on inner and/or outer surfaces or any combination thereof to promote desired properties such as adherence of materials to be engaged, radiopacity, and low friction between the device and the vessel wall or microcatheter lumen.

In summary, the invention is deliverable to the carotid artery or remote regions of the vasculature by gaining access through the use of a guidewire and microcatheter in the vasculature and subsequent deployment of the invention through the lumen of the microcatheter. During treatment of the vessel, the device is deployed downstream of the treatment site by withdrawing the microcatheter relative to the wire. Engagement occurs as the system composed of the invention and microcatheter is expanded against the vessel wall slightly offset of, and as mentioned above, downstream of the treatment site. After deployment of the filter device, treatment may commence and any foreign or naturally occurring materials which may result from the treatment will be captured by the device as the material flows freely with the stream of blood into the body of the filter device. Subsequent to completion of the treatment, removal of the material is accomplished by withdrawing the system into a guide catheter lumen through which the microcatheter is passed with or without simultaneously pulling fluid through the guide lumen.

Thus, it will be apparent from the foregoing that, while particular forms of the invention have been illustrated and described, various modifications can be made without departing from the spirit and scope of the present invention. Accordingly, it is not intended that the invention be limited, except as by the appended claims.

What is claimed is:

1. A medical device for capturing material within vasculature, comprising:
   an elongate member having a first end portion and a second end portion; and
   a body, the body including a first section defined by a plurality of first section members connecting the body to the elongate member and further including a second section connected to the first section, the second section defined by second section members configured to provide the body with a decreasing porosity in a direction superior to the first body section.

2. The device of claim 1, wherein the device is cut from a tube.

3. The device of claim 1, wherein the second section of the body is defined by a plurality of rings, each of the rings having a different longitudinal length.

4. The device of claim 3, wherein the plurality of rings are three in number.

5. The device of claim 1, further comprising a closed terminal end.

6. The device of claim 1, wherein the first section members are curved.

7. The device of claim 1, the second section of members defining at least one ring forming alternating V-patterns forming sixteen apices.

8. The device of claim 1, the first section of the body including a first series of members configured longitudinally inferior to a second series of members.

9. The device of claim 1, further comprising a terminal tip.

10. The device of claim 1, the body further including an inferior opening to an interior of the body, the body being attached to the elongate member such that the elongate member is attached to a side wall of the inferior opening.

* * * * *